United States Patent
Clapp et al.

(10) Patent No.: US 6,887,859 B2
(45) Date of Patent: May 3, 2005

(54) TOPICAL COMPOSITIONS CONTAINING FLUID-ABSORBENT SOLIDS AND ADHESIVE FLUIDS

(75) Inventors: Mannie Lee Clapp, Mason, OH (US); Rebecca Ann Taylor, Fairfield, OH (US); Colin Michael McHugh, Mason, OH (US); Jorge Max Sunkel, Cincinnati, OH (US); Timothy James Felts, Hamilton, OH (US); Edward Dewey Smith, III, Mason, OH (US); Scott William Syfert, Fort Mitchell, KY (US); Michael Joseph Roddy, Cincinnati, OH (US); Robert William Corkery, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 122 days.

(21) Appl. No.: 10/255,283

(22) Filed: Sep. 26, 2002

(65) Prior Publication Data

US 2003/0118533 A1 Jun. 26, 2003

Related U.S. Application Data

(60) Provisional application No. 60/325,023, filed on Sep. 26, 2001.

(51) Int. Cl.[7] .................... A61K 31/715; A61K 31/718; A61K 31/717; A61K 7/32
(52) U.S. Cl. ............................ 514/60; 514/57; 536/45; 536/56; 424/65
(58) Field of Search ....................... 514/60, 57; 536/45, 536/56; 424/65

(56) References Cited

U.S. PATENT DOCUMENTS

| | | | |
|---|---|---|---|
| 2,857,356 A | 10/1958 | Goodwin, Jr. | |
| 3,836,647 A | 9/1974 | Lange | |
| 4,145,308 A | * 3/1979 | Simoneau et al. | |
| 4,272,514 A | 6/1981 | Spence | |
| 4,485,092 A | 11/1984 | Ashton et al. | |
| 4,568,539 A | 2/1986 | Ashton et al. | |
| 4,650,670 A | 3/1987 | Callingham et al. | |
| 4,664,910 A | 5/1987 | Caserio et al. | |
| 4,822,596 A | 4/1989 | Callingham et al. | |
| 4,913,896 A | 4/1990 | Harvey | |
| 5,330,747 A | 7/1994 | Krzysik | |
| 5,338,535 A | 8/1994 | Berndt | |
| 5,451,610 A | 9/1995 | Krzysik | |
| 5,453,266 A | 9/1995 | Malka | |
| 5,460,804 A | 10/1995 | Krzysik | |
| 5,505,937 A | 4/1996 | Castrogiovanni et al. | |
| RE35,474 E | 3/1997 | Woodard et al. | |
| 5,780,020 A | 7/1998 | Peterson et al. | |
| 5,800,816 A | 9/1998 | Brieva et al. | |
| 5,861,143 A | 1/1999 | Peterson et al. | |
| 5,861,144 A | 1/1999 | Peterson et al. | |
| 5,861,146 A | 1/1999 | Peterson et al. | |
| 5,871,754 A | 2/1999 | Briggs et al. | |
| 5,885,599 A | 3/1999 | Peterson et al. | |
| 5,911,974 A | 6/1999 | Brieva et al. | |
| 5,959,019 A | 9/1999 | Riesgraf et al. | |
| 5,965,112 A | 10/1999 | Brieva et al. | |
| 5,985,298 A | 11/1999 | Brieva et al. | |
| 6,004,584 A | 12/1999 | Peterson et al. | |
| 6,019,962 A | 2/2000 | Rabe et al. | |
| 6,048,549 A | 4/2000 | Nitikhunkasem et al. | |
| 6,139,823 A | 10/2000 | Dreschler et al. | |
| 6,143,285 A | 11/2000 | Howard | |
| 6,274,152 B1 | 8/2001 | Brieva et al. | |

FOREIGN PATENT DOCUMENTS

| | | |
|---|---|---|
| CA | 711756 | 6/1965 |
| EP | 0 370 764 B1 | 5/1990 |
| EP | 0709083 | 9/2002 |
| JP | 2967140 B2 | 10/1999 |
| JP | 2001-288.030 | 10/2001 |
| WO | WO 95/04537 A1 | 2/1995 |
| WO | WO 96/03964 A1 | 2/1996 |
| WO | WO 99/04753 A1 | 2/1999 |

OTHER PUBLICATIONS

Shio (JP 2001288030 A2) (abstract sent).*
Sato et al (JP 04139110) (abstract sent).*

* cited by examiner

*Primary Examiner*—Samuel Barts
*Assistant Examiner*—Michael C. Henry
(74) *Attorney, Agent, or Firm*—Cynthia L. Clay; John M. Howell; Marianne Dressman

(57) ABSTRACT

Disclosed are topical compositions, including methods of applying those compositions to absorb sweat and sebum from the skin, wherein the compositions comprise (A) fluid-absorbent solids having a Water Absorption Value of at least about 0.5 grams/gram; (B) an adhesive fluid; and (C) a liquid carrier; herein the composition has an Average Wear Index Value of at least about 60%. The topical compositions provide effective delivery and deposition of the fluid-absorbent solid onto the skin from an extended wear composition.

48 Claims, No Drawings

TOPICAL COMPOSITIONS CONTAINING FLUID-ABSORBENT SOLIDS AND ADHESIVE FLUIDS

CROSS REFERENCE TO RELATED APPLICATION

This application claims the benefit of U.S. Provisional Application No. 60/325,023, filed Sep. 26, 2001.

FIELD OF THE INVENTION

The present invention relates to topical compositions containing moisture-absorbent solids in combination with an adhesive fluid. The topical compositions provide effective delivery and deposition of the fluid-absorbent solids onto the skin from an extended wear composition.

BACKGROUND OF THE INVENTION

Body powders of various types are well known for topical application to the skin to help provide absorption of sebaceous secretions and sweat. These products are commonly applied to the skin after showering or bathing, and are especially useful when applied to those areas of the skin that are more prone to perspiration wetness throughout the day. The applied powders readily adhere to the moist, recently-cleansed skin and thus provide a clean, dry feeling immediately after application. These products are often in the form of solid, flowable powders that contain fluid-absorbent particulates such as colloidal kaolin, starch, precipitated chalk, magnesium carbonate and other functionally similar materials.

Although body powders are effective in providing immediate fluid-absorbent benefits after application, they are not particularly effective over prolonged periods. Once applied to the skin, these powders almost immediately begin to fall off and wear away. Over extended periods of time, very little of the originally applied powder remains on the skin, so that perspiration wetness or sebum secretions that flow onto the surface of the skin over time are no longer absorbed and therefore are no longer effectively removed by the applied powders. As perspiration wetness and associated oils remain and accumulate on the surface of the skin, the skin begins to feel oily and dirty.

One method of improving the performance of body powders has been to reapply the powders to the desired area of the skin as needed throughout the day to help maintain the clean, dry feeling associated with the application of such fluid-absorbent materials to the skin. For most people, however, frequent reapplication of a body powder throughout the day is neither desirable nor practical. Even a single application of a body powder tends to be messy, especially when applied to those areas of the skin that come in contact with clothing. Moreover, these powders tend to rub off more easily when the skin comes in contact with clothing, leaving the skin unprotected with fluid-absorbent body powder, much of which deposits onto the clothing leaving a white or chalking appearing residue on the clothing.

Still other methods of improving the extended wear characteristics of common body powders involves the addition of adhesive materials to the powders such as water-insoluble metallic soaps (e.g., zinc and magnesium stearates), emollients such as cetyl or stearyl alcohol and glyceryl monostearate, petroleum jelly, mineral oil, and similar other materials. These added adhesives help improve deposition and adherence of the powders to the skin, thus improving the extended wear characteristics of the body powder. Although these adhesives provide extended wear properties to the product, the powder still tends to wear away shortly after application, readily sloughs off and forms a visible residue on clothing, and is messy to apply. Many of these adhesives can also interfere with the fluid-absorbent efficacy of the body powders, as well as provide for poor skin feel or other undesirable cosmetic characteristics.

It has now been found that fluid-absorbent solids can be selected and formulated within a liquid composition to provide effective deposition of the solids onto the skin, while also providing adhesion and maintenance of those solids onto the skin over prolonged periods of time, along with desirable skin feel and other cosmetic characteristics. It has been found that such a formulation can be achieved by preparing a topical liquid composition comprising fluid-absorbent solids having a Water Absorption Value as defined herein of at least about 0.5 grams/gram, an adhesive fluid such as a solubilized adhesive material, and a liquid carrier, wherein the liquid composition has an Average Wear Index as defined herein of at least about 25%. These liquid compositions are easier and less messy to apply than conventional body powders, can result in less visible residue on surrounding clothing, and can provide improved fluid-absorption benefits as compared to similar other materials containing other well known adhesives.

It is therefore an object of the present invention to provide a body powder formulation that provides moisture and other fluid absorbing benefits over prolonged periods of time. It is a further object of the present invention to provide such a formulation from a liquid composition that is less messy to apply than conventional dry powders and has desirable skin feel and cosmetic benefits. It is still a further object of the present invention to provide such a liquid composition by combining a suitable liquid carrier, an adhesive fluid, and certain moisture-absorbent solids, to provide an extended wear product.

SUMMARY OF THE INVENTION

The present invention relates to topical compositions that comprise fluid-absorbent solids having a Moisture Absorption Value as defined herein of at least 0.5 grams/gram, an adhesive fluid, and a suitable liquid carrier, wherein the topical composition provides extended wear benefits characterized by an Average Wear Index as defined herein of at least about 25%.

It has been found that the topical liquid compositions of the present invention provide effective delivery and deposition of fluid-absorbent solids onto the skin, while also providing adhesion and maintenance of those solids onto the skin over prolonged periods of time. These compositions when applied topically provide absorption of sweat and sebum from the skin, and thus provide effective removal of such fluids from the skin. These topical fluid-absorption benefits can be maintained over prolonged periods of time, and thus provide topical fluid-absorption benefits throughout the day after just a single application. These compositions can also provide other extended wear benefits as well as the effective delivery of fluid-absorbent solids, all from a liquid or rather than a powder base matrix.

DETAILED DESCRIPTION

The topical compositions of the present invention comprise fluid-absorbent solid particulates, an adhesive fluid, and a liquid carrier. These and other essential limitations of the compositions and methods of the present invention, as well as many of the optional ingredients suitable for use herein, are described in detail hereinafter.

The term "adhesive" and as used herein, unless otherwise specified, refers to any solid material that can be solubilized within the compositions of the present invention, and that helps provide the composition with an Average Wear Index as defined herein of at least about 25%. The term "adhesive fluid" therefore refers to the adhesive material within the compositions, wherein the adhesive is solubilized and in liquid form within the compositions.

The term "fluid-absorbent solid" as used herein, unless otherwise specified, refers to those materials that absorb moisture or other fluids such as sebaceous secretions and moisture-containing sweat from the surface of the skin.

The term "anhydrous" as used herein, unless otherwise specified, refers to those compositions or materials containing less than about 10%, more preferably less than about 5%, even more preferably less than about 3%, even more preferably zero percent, by weight of water. The topical compositions of the present invention can be aqueous or anhydrous, but are preferably anhydrous.

The term "volatile" as used herein, unless otherwise specified, refers to those materials that have an average boiling point at one (1) atmosphere of pressure (atm) of less than about 250° C., more typically less than about 235° C. at one (1) atm.

The term "ambient conditions" as used herein refers to surrounding conditions at one atmosphere of pressure, 50% relative humidity, and 25° C.

All viscosity values as described herein, unless otherwise specified, are expressed in terms of centistokes (cs) and are determined or otherwise measure by a Brookfield DV-II+ viscometer at 1 rpm at 25° C.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

The topical compositions and methods of the present invention can comprise, consist of, or consist essentially of the essential elements and limitations of the invention described herein, as well as any additional or optional ingredients, components, or limitations described herein or otherwise useful in personal care compositions intended for topical application to the skin.

Product Form

The topical compositions of the present invention can be formulated in any of a variety of product forms, so long as the product forms contain the essential ingredients as defined herein. These products are typically and preferably in liquid or semi-liquid form, more preferably in liquid form. Non-limiting examples of such product forms include soft solids, lotions or creams, aerosol sprays, aerosol foams, pump sprays, and so forth.

These products can be prepared and used as either leave-on, rinse-off or wipe-off formulations, but are preferably prepared and used as leave-on formulations. These products can be formulated to deliver any of a variety of personal care or cosmetics functions in addition to the fluid-absorbing functions, including personal care or cosmetic functions associated with color or other cosmetics, shampoos or other hair care products, skin cleansing products, topical pharmaceuticals, topical skin active compositions, or any other product form that provides for topical delivery of any suitable skin active agent or benefit.

The topical compositions of the present invention, under ambient conditions, are preferably in liquid form and have a preferred viscosity of less than 100,000 centistokes, more preferably from about 10 to about 50,000 centistokes, even more preferably from about 20 to about 30,000 centistokes, as measured at 25° C., although the selected viscosity of the composition will vary greatly depending upon variables such as product form, selected ingredients, intended product use, and so forth.

Adhesive Fluid

The topical compositions of the present invention comprise an adhesive material that is suitable for topical application to the skin. Any such adhesive material, which can include both solid and liquid adhesives prior to formulation, is suitable for use herein provided that it ultimately forms a dispersed liquid within the composition, or is otherwise solubilized within the liquid carrier component of the composition, to thus form an adhesive fluid within the composition of the present invention. The adhesive fluid can include conventional adhesive materials such as those associated with bandages, pharmaceutical patches, paper products, etc., or can also include various film-forming polymers that do not otherwise inherently deliver tack or stickiness, but nonetheless provide the composition with enhanced Average Wear Index values as defined herein.

The adhesive fluid for use in the compositions of the present invention preferably comprises an adhesive material that is inherently solid under ambient conditions, but has been solubilized in the liquid carrier component of the topical compositions of the present invention. These adhesive materials are preferably solid polymeric materials, silicone-containing or otherwise, that are solubilized and in liquid form within the composition of the present invention. Most preferred are silicone resin copolymer adhesives and adhesive materials comprising a organosiloxane resin in combination with a diorganosiloxane fluid. Each of these preferred adhesive fluid materials is described in more detail hereinafter Other adhesive materials for use herein include well known adhesive materials such as those categorized as acrylic, urethane, cyanoacrylates, silicone (other than those otherwise described herein), polyolefins (vinylics) and combinations thereof.

Non-limiting examples of other adhesive materials suitable for use in the compositions of the present invention include Amphomer LV-71 (Octylacrylamide/Acrylates/Butylaminoethyl methacrylate Copolymer); Luvimer 100P (acrylates copolymer); SA70 in D5 (Polyacrylates-g-polysiloxane, cyclomethicone (soluntion w/75% D5); Luviskol VA73W (VP/VA Copolymer (solution with 50% copolymer)); Pemulen TR2 (Acrylates/C10–30 Alkyl Acrylate Crosspolymer); Diahold JG (60% in IDD) (Butyl Acrylate/Ethylhexyl Methacrylate Copolymer); Luviskol VA 64W (VP/VA Copolymer); Ganex V220 (40% in IDD) (Eicosene Copolymer, Isododecane); Luviskol K30 (PVP); Bio PSA 4500 (58% in IDD) (Trimethylated silica treated with dimethyl siloxane, Isododecane); Luviskol Plus (Polyvinylcaprolactam); Luviflex Soft (Acrylates Copolymer); Polyderm PE/PA (Polyurethane); Luviskol K90 (PVP); Dermacryl LT (Acrylates/Octylacrylamide Copolymer); AMP-Regular (Aminomethyl propanol); Luviset PUR (Polyurethane-1); Bio PSA 4500 (40% in IDD) (Trimethylated silica treated with dimethyl siloxane, Isododecane);

Silicone Resin Copolymer Adhesives

The topical compositions of the present invention include adhesive materials in the adhesive fluid component, wherein the adhesive material is a silicone resin copolymer derived from the condensation or other functionally similar reaction or combination of an organosiloxane resin with a diorganopolysiloxane fluid. These silicone resin copolymers are known for use as adhesives in various consumers' products and applications, and are now formulated into the compositions of the present invention for the purpose of improving the deposition or adherence of fluid-adsorbent solids onto the skin.

The concentration of the silicone resin copolymer in the topical compositions of the present invention varies considerably depending upon other ingredients in the composition as well as the intended product form. Generally, silicone resin copolymer concentrations range from about 0.05% to about 40%, preferably from about 2% to about 35%, even more preferably from about 15% to about 35%, by weight of the topical composition.

The silicone resin copolymers for use as an adhesive material herein preferably have an average molecular weight of at least about 15,000, more preferably from about 15,000 to about 4 million, even more preferably from about 100,000 to about 3 million.

It has been found that the silicone resin copolymers as defined herein provide effective substantivity and extended cosmetic wear characteristics when formulated into the topical compositions of the present invention, regardless of whether they form a thick polymeric film over the applied surface area. It is believed that the selection of these particular silicone resin copolymers allows for improved adherence and deposition of the fluid-absorbent solids onto skin, without the need for such heavy polymeric films over the applied areas to keep the solid particulates deposited on and adhered to the intended site of application.

The silicone resin copolymers for use as an adhesive material herein can be prepared by any known or otherwise effective method or chemistry for making such materials, non limiting examples of which include co-hydrolysis or by reacting triorganosilanes or other similar siloxanes with a silica hydrosol. The silicone resin copolymers are generally prepared by mixing and heating together an organosiloxane resin, diorganosiloxane fluid, and catalyst, at a temperature of above about 100° C., until the desired adhesive character of the resulting silicone resin copolymer is obtained. Mixing can be facilitated by the use of mutual solvents such as benzene, toluene, xylene, naptha, mineral spirits or other suitable solvent, which is subsequently removed from the mixture during the heating and mixing process.

The silicone resin copolymers for use in the topical compositions of the present invention are preferably prepared by heating a mixture of (1) from about 45% to about 75% by weight of the organosiloxane resin as a condensation product of $SiO_2$ and $R_3(SiO)_{0.5}$ units, wherein each R group is independently selected from methyl, ethyl, propyl or vinyl radicals, and the ratio of $SiO_2$ units to $R_3(SiO)_{0.5}$ units in the organosiloxane resin is from about 0.6 to about 1.0; (2) from about 25% to about 55% by weight of a hydroxyl end-blocked diorganopolysiloxane fluid having a viscosity in the range of from about 100 to about 100,000 cs at 25° C., wherein the organic substituents on the diorganosiloxane fluid are independently selected from methyl, ethyl, or vinyl radicals; and (3) from about 0.001% to about 5% by weight of a suitable catalyst, preferably an aliphatic organic amino compound selected from primary amines, secondary amines, tertiary amines, carboxylic acid salts of the above amines and quaternary ammonium salts. The mixture of materials is heated at a temperature above about 100° C. until the desired adhesive character of the resulting silicone resin copolymer is obtained.

Organosiloxane resins suitable for use in preparing the silicone resin copolymers for use herein are therefore those that preferably contain $SiO_2$ units and $R_3(SiO)_{0.5}$ units (triorganosilyl) in a molecular ratio of from about 0.6 to about 1.0. Suitable triorganosilyl units for use in such organosiloxane resins include trimethylsilyl, triethylsilyl, methylmethylpropylsilyl, dimethylvinylsilyl, and combinations thereof. Preferred are trimethylsilyl units.

Diorganosiloxanes fluids suitable for use in preparing the silicone resin copolymers include hydroxyl end blocked diorganosiloxane polymers. The diorganosiloxanes are preferably linear polymers that contain only diorganosiloxane units, but can include small amounts of other materials such as triorganosiloxane units, monorganosiloxane units and $SiO_2$ units in minor amounts, typically less than about 1.0% by weight of the diorganosiloxane fluid, provided that the diorganosiloxane fluid remain hydroxyl end blocked to allow for the desired condensation reaction with the organosiloxane resin to form the silicone resin copolymer.

The organic substituents on the diorganosiloxane fluids for use in preparing the silicone resin copolymer can be any one or more of methyl, ethyl or vinyl radicals. Non-limiting examples of suitable diorganosiloxane fluids include ethylmethylpolysiloxane, copolymers of dimethylsiloxane and methylvinylsiloxane units, and mixtures of polymers or copolymers so long as such materials are hydroxyl end blocked. The viscosity of the diorganosiloxane polymer is preferably at least about 100 centistokes, and typically at least about 100,000 centistokes, as measured at 25° C., although it is understood that the diorganosiloxane fluid for use in this context can be substituted with a diorganosiloxane solid having a viscosity well beyond 10 million centistokes as measured at 25° C.

The organic amino compound for use as a catalyst in preparing the silicone resin copolymer includes any aliphatic hydrocarbon amine; alkanol amine; carboxylic acid salt thereof; and tertiary amine such as trimethylamine, tributylamine, methyldiproppylamine, and quaternary ammonium salts. This includes primary amines such as hexylamine, butanolamine, and butylamine; secondary amines such as diethylamine, diethanolamine, ethylamylamine and propylhexylamine; tertiary amines such as trimethylamine, tirbutylamine, methyldipropylamine, tirpropanolamine, and methylpropylhexylamine; and quaternary ammonium salts such as tetramethylammonium acetate and methylethyldibutylammoniumchloride, including quaternary ammonium emulsifying agents sold under various trade names, such as dioctadecyldimethylammonium chloride. In addition, any carboxylic acid salt of the amines, such as diethylamine acetate, butylamine octoate and trimethylamine laurate can be used. Tertiary amines are preferred, especially tertiary aliphatic amines.

Organosiloxane Resin Adhesives

The topical compositions of the present invention also include adhesive materials that contain an organosiloxane resin, wherein the resin is used in combination with a liquid carrier component comprising a diorganopolysiloxane fluid. This preferred adhesive material can be used alone or in combination with the above-described organosiloxane resin copolymer or other similar adhesive materials.

The organosiloxane resin adhesive is preferably used in the composition of the present invention such that the weight ratio of the resin to the diorganopolysiloxane fluid is from about 1:5 to about 10:1, more preferably from about 1:1 to about 5:1, even more preferably from about 1:1 to about 3:1, and wherein the total concentration of the organosiloxane resin and the diorganopolysiloxane fluid ranges from about 10% to about 40%, more preferably from about 15% to about 30%, even more preferably from about 20% to about 30%, by weight of the composition.

The organosiloxane resin adhesive for use in the compositions of the present invention include combinations of $R_3SiO_{1/2}$ (M units), $R_2SiO$ (D units), $RSiO_{3/2}$ (T units), $SiO_2$ (Q units) units in ratios to each other that satisfy the relationship $RnSiO_{(4-n)/2}$ where n is a value between 1.0 and 1.50 and R is a methyl group. Note that a small amount, up to 5%, of silanol or alkoxy functionality may also be present in the resin structure as a result of processing. The organosiloxane resins are solids at about 25° C. and have an average molecular weight that generally ranges from about 1,000 to about 10,000 grams/mole.

Preferred organosiloxane resins for use in the compositions of the present invention are those that contain repeating monofunctional or $R_3SiO_{1/2}$ (M units) and quadrafunctional or $SiO_2$ (Q units), otherwise known as "MQ" resins as described in U.S. Pat. No. 5,330,747 (Krzysik), which descriptions are incorporated herein by reference. Examples of highly preferred organosiloxane resins are those in which the ratio of "M" to "Q" functional units is about 0.5 and the value of n is 1.5, non-limiting examples of which are commercially available from Wacker Silicones Corporation of Adrian Mich. (e.g., Wacker 803 and 804) and the General Electric Company (e.g., G. E. 1170-002).

Other suitable organosiloxane resins suitable for use herein include functionalized silicone resins, an example of which includes silicone ester waxes comprising moieties of the general formula:

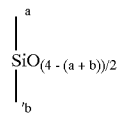

wherein R is an organic radical, R' is a carboxylic acid ester, "a" and "b" are integers independently either 1 or 2 wherein a+b equals 2 or 3.

The diorganopolysiloxane fluid for use in combination with the organosiloxane resin can be any diorganopolysiloxane fluid that can be solubilized within or compatibly dispersed throughout the composition and that is otherwise compatible with the other essential ingredients of the composition. In this context, and for purposes of defining the compositions of the present invention, the diorganosiloxane fluid is considered part of the liquid carrier component of the compositions of the present invention. It is understood, however, that the diorganosiloxane fluid can still be used in the topical compositions even when the adhesive material does not contain an organosiloxane resin, and conversely, that the organosiloxane resin can still be used in the composition without the organosiloxane fluid, but that it is highly preferred that when such resin materials are used, they are used in combination with the diorganosiloxane fluid.

When used in combination with an organosiloxane resin, the concentration of the diorganopolysiloxane fluid in the topical composition of the present invention depends upon the total resin/fluid concentration and the relative weight ratios of the two, but will generally range from about 3% to about 15%, more typically from about 5% to about 10%, even more typically from about 5% to about 8%, by weight of the composition.

When used in combination with an organosiloxane resin, the diorganopolysiloxane fluid has a preferred viscosity of from about 100,000 to about 25,000,000 centistokes (cSt) at 25° C. and preferably forms a solution with the organosiloxane resin and any other liquid carrier materials in the composition.

The diorganopolysiloxane fluid for use herein comprises repeating units that correspond to the formula $(R_2SiO)$, where R is a monovalent hydrocarbon radical containing from 1 to 6 carbon atoms, preferably R is selected from methyl, ethyl, propyl, isopropyl, butyl, isobutyl, t-butyl, amyl, hexyl, vinyl, allyl, cyclohexyl, phenyl, fluoroalkyl and mixtures thereof. The diorganopolysiloxane fluid may contain one or more of these hydrocarbon radicals as substituents on the siloxane polymer backbone. The diorganopolysiloxane fluid may be terminated by triorganosilyl groups of the formula $(R'_3Si)$ where R' is a radical selected from monovalent hydrocarbons containing from 1–6 carbon atoms, hydroxyl groups, alkoxyl groups and mixtures thereof.

Non limiting examples of preferred diorganopolysiloxane fluids for use herein include poly(dimethylsiloxane) [PDMS] materials such as those available from General Electric as SE30, SE72, SE84, Viscasil® 100M, and Baysilone Fluid M 500,000.

Liquid Carrier

The compositions of the present invention comprise a liquid carrier suitable for topical application to the skin that is also compatible with the essential materials selected for use herein. The carrier is a liquid under ambient conditions or is otherwise in liquid form as formulated within the compositions, and solubilizes the adhesive material in the composition or otherwise helps to maintain the adhesive material as solubilized within the composition. The liquid carrier can be aqueous or anhydrous, and includes carrier liquids that are silicone-containing or non silicone-containing, volatile or non-volatile. Anhydrous fluids are preferred.

The liquid carrier for use in the composition of the present invention preferably includes at least one volatile carrier liquid at a concentration of from about 10% to about 90%, preferably from about 20% to about 80%, more preferably from about 40% to about 60%, by weight of the composition.

Volatile hydrocarbons suitable for use as a liquid carrier in the topical compositions herein include those hydrocarbons having boiling points in the range of from about 60° C. to about 260° C., more preferably volatile hydrocarbons having from about $C_8$ to about $C_{20}$ chain lengths, more preferably $C_8$ to $C_{20}$ isoparaffins. Preferred isoparaffins for use herein include isododecane, isohexadecane, isoeocosane, 2,2,4-trimethylpentane, 2,3-dimethylhexane and combinations thereof. Most preferred is isododecane.

Volatile silicones suitable for use as a liquid carrier in the topical compositions include those volatile silicones as described in Todd et al., "Volatile Silicone Fluids for Cosmetics", Cosmetics and Toiletries, 91:27–32 (1976), which descriptions are incorporated herein by reference. The volatile silicone liquid can be linear, cyclic or branched, but is preferably a cyclic silicone having from about 3 to about 7, more preferably from about 4 to about 5, silicon atoms. Most preferably are those which conform to the formula:

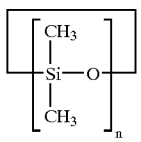

wherein n is from about 3 to about 7, preferably from about 4 to about 5, most preferably 5. Suitable volatile silicones for use herein include, but are not limited to, Cyclomethicone D-5 (commercially available from G. E. Silicones); Dow Corning 344, and Dow Corning 345 (commercially available from Dow Corning Corp.); GE 7207, GE 7158 and Silicone Fluids SF-1202 and SF-1173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V (available from Mazer) and combinations thereof. Cyclopentasiloxane is most preferred among the volatile silicone liquids.

The liquid carrier for use in the compositions of the present invention can also include various other silicone-containing, volatile and non-volatile, diorganopolysiloxanes fluids that comprise repeating units corresponding to the formula ($R_2SiO$), where R is a monovalent hydrocarbon radical containing from 1 to 6 carbon atoms, preferably R is selected from methyl, ethyl, propyl, isopropyl, butyl, isobutyl, t-butyl, amyl, hexyl, vinyl, allyl, cyclohexyl, phenyl, fluoroalkyl and mixtures thereof. The fluid diorganopolysiloxane polymers may contain one or more of these hydrocarbon radicals as substituents on the siloxane polymer backbone. The diorganopolysiloxanes may be terminated by triorganosilyl groups of the formula ($R'_3Si$) where R' is a radical selected from monovalent hydrocarbons containing from 1–6 carbon atoms, hydroxyl groups, alkoxyl groups and mixtures thereof. Polydimethylsiloxanes are preferred, especially linear dimethicones having a viscosity of from about 5 cs to about 500,000 cs, preferably from about 10 cs to about 200,000 cs, as measured at 25° C.

The liquid carrier preferably comprises a residue masking agent. These masking agents are non-volatile liquids that when formulated into the composition help reduce the visible residue on the skin associated with the use of various solid materials, especially the fluid absorbent solids as described hereinafter. The masking agent can be a silicone-containing material as described herebefore, or an organic or non-silicone containing non-volatile fluid.

As stated earlier, many of these silicone fluids are preferably used in combination with those adhesive materials containing an organosiloxane resin.

Fluid Absorbent Solids

The topical compositions of the present invention comprise fluid-absorbent solids suspended or dispersed throughout the compositions. The fluid-absorbent solids can be any material that remains solid within the composition and provides fluid absorption properties when applied topically to the hair, nails or skin, wherein the requisite fluid absorption properties of the fluid-absorbent solid are determined by, and correlates with, a Moisture Absorption Value of at least 0.5 gram/gram as measured in accordance with the Moisture Absorption Test as defined hereinafter.

The fluid-absorbent solids for use in the compositions of the present invention include moisture-absorbent materials such as silicas (or silicon dioxides), silicates, carbonates, various organic copolymers, and combinations thereof. The silicates are most typically those formed by reaction of a carbonate or silcate with an alkali metal, alkaline earth metal, or transition metal, specific non-limiting examples of which include calcium silicate, amorphous silicas (e.g., precipitated, fumed, and colloidal), calcium carbonate (e.g., chalk), magnesium carbonate, zinc carbonate, and combinations thereof. Non-limiting examples of some suitable silicates and carbonates for use herein are described in Van Nostrand Reinhold's Encyclopedia of Chemistry, $4^{th}$ edition, pages 155, 169, 556, and 849 (1984), which descriptions are incorporated herein by reference. Absorbent powders are also described in U.S. Pat. No. 6,004,584 (Peterson et al.), which description is incorporated herein by reference.

Other fluid-absorbent solids suitable for use herein include kaolin, (hydrated aluminum silicates), mica, talc (hydrated magnesium silicates), starch or modified starch, microcrystalline cellulose (e.g., Avicel from FMC Corporation), fluid-absorbent polyethylenes or other functionally similar fluid-absorbent polymer, any other silica-containing or non-silica-containing powder suitable for absorbing moisture or oil from the applied surface of the body.

The average particle size of the fluid-absorbent solids for use in the compositions is preferably less than about 250 nm, more preferably less than 200 nm. It has been found that the visible residue of such solid materials is greatly reduced when the average particle size of the solid materials is reduced as noted above. Typical processes used to reduce the particle size sufficiently include wet milling and controlled flow cavitation. In a wet milling process, a slurry is prepared with the particle to be reduced and water or other suitable fluid. The slurry is placed in a stirred media mill chamber with potential dispersants. The dispersants could be ceramic, stainless steel, polymeric coated materials or other and may range in size from 50 microns to 3 millimeters. The tip speed of the rotor arms may range between 5 to 20 meters per second and total particle residence time may vary from 30 to 300 seconds. Netzsch is a manufacturer of these types of stirred media mills.

Among the fluid-absorbent solids for use herein, highly preferred are those that have a Moisture Absorption Value of at least about 0.5, preferably from about 1.0 to about 5.0, even more preferably from about 3.0 to about 5.0, grams of moisture absorption per gram of fluid-absorbent solid as measured in accordance with the Moisture Absorption Test as described herein. These Moisture Absorption Values have been found to correlate with the ability of the topical compositions of the present invention containing such materials to provide moisture, sweat and/or sebum absorption from the applied surface over extended periods of time after topical application.

The concentration of fluid-absorbent solids in the composition preferably ranges from about 0.1% to about 20%, more preferably from about 0.5% to about 10%, even more preferably from about 2% to about 8%, by weight of the composition.

It has been found, therefore, that the fluid-absorbent solids as described herein can be formulated into the compositions of the present invention to provide long lasting or enduring moisture, sebum and/or sweat absorption from the skin or other applied area after application. It is believed that the adhesive fluid material as described herein provides improved deposition and adherence of the fluid-absorbent solids to the applied surface area, even when such fluid-absorbent solids are formulated into the liquid embodiments of the present invention, to thus provide long lasting or enduring moisture and other fluid-absorption benefits on the applied areas of the body.

Moisture Absorption Test

The fluid-absorbent solids for use in the compositions of the present invention must have a minimum Moisture Absorption Value of at least about 0.5 gram/gram, wherein the Moisture Absorption Value is determined in accordance with the following Moisture Absorption Test. A powder chamber (Kruss Fiber Cell) and two filter papers (Kruss filter paper, part # FL12PLP) are preweighed on a balance and balance tared. One of the filter papers is then placed at the bottom of the powder chamber. The sample of absorbent powder to be tested is then packed into the chamber using a spatula. The mass of powder loaded into the chamber will vary depending upon the density of the powder, but will most typically range from about 0.50 grams to about 3.5 grams of powder packed into the powder chamber. A second filter paper is then placed on top of the packed powder and the screw cap for the chamber is placed on the chamber. The chamber knob is then rotated by hand until the powder is firmly packed and the knob can no longer be rotated manually. The powder chamber is then placed within a Kruss Tensiometer. The Tensiometer glass dish is then filled with distilled water and positioned on the stage device. The Tensiometer is then turned on and the stage is raised to just below the powder chamber so that the powder does not yet contact the distilled water in the dish. The Tensiometer is then balanced and allowed to tare. The Tensiometer is then turned off and the stage is raised until the powder chamber is immersed 9 mm in the distilled water. The mass of the powder sample is measured every fifteen seconds until the mass has reached equilibrium and no longer fluctuates drastically.

The Water Absorption Value is then determined for any given sample by calculating the difference between the mass of the powder chamber at 15 seconds and the mass of the powder chamber at the equilibrium point, divided by the mass of powder initially loaded into the chamber, all in accordance with the equation.

Optional Ingredients

The topical compositions of the present invention may further comprise other optional ingredients that may modify the physical, chemical, cosmetic or aesthetic characteristics of the compositions or serve as additional "active" components when deposited on the skin. The compositions may also further comprise optional inert ingredients. Many such optional ingredients are known for use in personal care compositions, and may also be used in the topical compositions herein, provided that such optional materials are compatible with the essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. Non limiting examples of such optional ingredients include preservatives (e.g., propyl paraben), deodorants, antimicrobials, fragrances, deodorant perfumes, coloring agents or dyes, thickeners, sensates, sunscreens, surfactants or emulsifiers, gellants or other suspending agents, pH modifiers, co-solvents or other additional solvents, emollients, pharmaceutical actives, vitamins, and combinations thereof.

Other optional ingredients include silicone elastomer powders and fluids to provide any of a variety of product benefits, including improved product stability, application cosmetics, emolliency, and so forth. The concentration of the silicone elastomer in the composition preferably ranges from about 0.1% to about 20%, more preferably from about 0.5% to about 10%, by weight of the composition. In this context, the weight percentages are based upon the weight of the silicone elastomers material itself, excluding any silicone-containing fluid that typically accompanies such silicone elastomers materials in the formulation process. The silicone elastomers suitable for optional use herein include emulsifying and non-emulsifying silicone elastomers, non-limiting examples of which are described in U.S. Ser. No. 09/613,266 (assigned to The Procter & Gamble Company), which description is incorporated herein by reference.

Other optional materials include perfumes or fragrances, including deodorant and pro-perfumes, concentrations of which optionally typically range from about 0.1% to about 5%, more typically from about 0.5% to about 4%, by weight of the composition. It has been found that the fragrance expression or longevity is extended when such perfumes or fragrances are formulated into the composition. It is believed that the adhesive fluids as described herein help extend perfume expression or longevity within the composition.

The optional materials include pigments, although the the present invention includes embodiments that are substantially free of pigments. In this context, the term "substantially free" means that such embodiments contain less than about 1.0%, preferably less than 0.1%, most preferably zero percent, by weight of pigments.

The optional ingredients as described herein shall specifically exclude, however, any essential ingredient or material as otherwise described or defined herein.

Optional Solid Particulates

The compositions of the present invention may further comprise solid particulates other than and in addition to the fluid-absorbent solids described herein. These optional solid particulates can be dispersed throughout the composition to allow for deposition onto the hair, nails or skin after topical application of the composition. The optional solid particulate can be any skin active agent or other material known for or otherwise useful in application to and deposition onto the hair, nails or skin. Such solid particulates include materials such as emollients, perfumes, vitamins, sunscreens, pigments or colorants, pharmaceuticals or other skin active agents, or any other solid material that provides a cosmetic, skin active, or other consumer desirable benefit when applied to and deposited on the hair, nails, or skin.

The weight ratio of the fluid adhesive material to the optional solid particulates is preferably selected from within the range of from about 5:1 to about 1:20, more preferably from about 4:1 to about 1:15. The concentration of the solid particulates in the composition will vary considerably depending upon variables such as the desired product form, the adhesive fluid concentration, the optional solid particulate selected and its intended benefit, and other similar variables.

Extended Wear

The topical compositions of the present invention deliver extended wear benefits as characterized by an Average Wear Index as described hereinafter. These index values are determined for any given composition in accordance with the supporting methodologies described hereinafter. All measurements associated with the supporting methodologies are made under ambient condition, unless otherwise specified.

The topical compositions of the present invention preferably provide an Average Wear Index (AWI) of at least about 25%, more preferably at least about 50%, even more preferably from about 75% to 100%, wherein the Average Wear Index is determined by the test methodology described hereinafter. The AWI value is a measure of the amount or percentage of a topically applied product that remains on an applied surface over an extended period of time falling or rubbing off. Thus, higher AWI values correlate with extended wear.

The Average Wear Index is therefore an indirect measure of the extended wear properties of the topical compositions of the present invention, and is determined by the following Methodology. Equipment and material for use in the test method include a balance (0.1 mg readability), x-ray fluorescence (XRF) cups for film mounting (Chemplex Cat. 1095, 45 mm diameter), COFFI film (plasticized collagen, Butcher & Packer, COFFI-11), weights, and cotton fabric (e.g., T-shirt cotton). Product testing is performed in an environmentally controlled room at 75° F., 50% relative humidity.

The test methodology is initiated by cutting a COFFI film to the appropriate size for mounting with the XRF cups. The XRF cups are prepared by snapping the COFFI film in place, and allowing the cup/film combination to remain in place within the controlled room environment for 24 hours before product sampling.

Immediately after the 24-hour conditioning period described above, the initial weight of the film-cup combination is weighed. The top of the COFFI film is coated with about 50 mg of the sample composition using a brush to spread the product over the film surface. The weight of the cup-film-coating is weighed and a final sample weight determined. The applied product on the film is allowed to dry for at least about 24 hours. When the coating is dry, it is weighed and a dry sample weight determined. The cup is inverted onto a cotton fabric such that the sample coating is facing downward and is in contact with the fabric. The cotton fabric is placed over a 100% plasitcized polyurethane product to add suppleness to the surface of the cotton fabric facing the dried coating. A 500 gram weight is place on the on top of the cup to apply pressure to the interface between the dried coating and the cotton fabric.

The cup is then rotated 360 degrees. The cup-film-coating is then weighed again, and a final product weight determined. The 500 gram weight is then replaced with a 1.5 kg weight before rotating the cup another 100 degrees. The cup-film-coating is then weighed again, and the final weight determined.

An initial wet sample weight of the coated material (prior to drying) is calculated as the difference between the initial weight of the cup-film and the initial weight of the cup-film-coating prior to drying. An initial dry sample weight is calculated as the difference between the initial weight of the cup-film and the initial weight of the cup-film-coating immediately after drying. The amount of coated product lost after rotation under the 500 gram and 1.5 kg weights is determined by similar calculation. An average of the amount of product lost under the two rotations together is determined, and an average value taken, and then converted to a percentage of the originally dried coating removed during rotation. This percentage is then subtracted from 100% to obtain a Wear Index Value.

The above-described sequence is then repeated for a total of two or more runs for each product sample. An average of all Wear Index Values from the repeated runs is obtained and thus represents the Average Wear Index Value as used herein to characterize the topical compositions of the present invention.

Method of Use

The topical compositions of the present invention are applied topically to the desired area of the hair, skin or nails in an amount sufficient to provide effective delivery of the desired fluid-absorbent solid to the applied surface. The compositions can be applied to the desired area of the hair, skin or nails and allowed to remain as a leave-on product, or the compositions can be rinsed away with water or wiped off of the applied surface. The compositions are preferably used as leave-on applications, i.e., not rinsed or wiped off within 6 hours, preferably with 24 hours, of application.

The topical composition of the present invention includes leave-on compositions that are applied to the skin to provide sebum and/or sweat absorption, more preferably once daily, especially after showering or bathing.

The topical compositions of the present invention can also be applied to the body, wherein the composition is preferably not applied to the head or neck, for the purpose of absorbing perspiration wetness and/or sebum from the skin after application, preferably over an extended period of time of at least about 4 hours, preferably from about 6 hours to about 24 hours.

Method of Manufacture

The topical compositions of the present invention may be prepared by any known or otherwise effective technique, suitable for making and formulating the desired product form. Specific non-limiting examples of such methods as they are applied to the compositions of the present invention are described in the examples set forth below.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are active concentrations (not inert carriers, solvents, etc.) by weight of the total composition, unless otherwise specified. To the extent that product concentrations do not add up to 100% for any particular example, the deficit is from excipient materials such as inert carriers, solvents, and so forth.

The topical compositions described below provide topical deposition and adherence of various fluid-absorbent solids onto the skin. The compositions have desirable skin feel and other cosmetic characteristics. Each composition also provides improved fluid-absorbing characteristics (Moisture Absorption Value of the absorbent solid of at least 0.5 gram/gram) and extended wear properties (Average Wear Index of at least 25%).

TABLE 1

| | Topical Liquid Compositions | | | | | |
|---|---|---|---|---|---|---|
| Ingredient | | 1.1 | 1.2 | 1.3 | 1.4 | 1.5 |
| Luvimer 100P | Acrylates Copolymer | 6.0 | — | — | — | — |
| Luviskol VA 64W | VP/VA Copolymer | — | 6.0 | — | — | — |

TABLE 1-continued

Topical Liquid Compositions

| Ingredient | | 1.1 | 1.2 | 1.3 | 1.4 | 1.5 |
|---|---|---|---|---|---|---|
| Luviskol VA73W | VP/VA Copolymer | — | — | 6.0 | — | — |
| Luviskol K30 | PVP | — | — | — | 6.0 | — |
| Luviskol Plus | Polyvinylcaproalctam | — | — | — | — | 6.0 |
| Silica Shells | Silica | 2.0 | 2.0 | 2.0 | 2.0 | 2.0 |
| Talc USP | Talc | 18.0 | 18.0 | 18.0 | 18.0 | 18.0 |
| Water | — | 73.8 | 68 | 68 | 73.7 | 65 |

Each of the Table 1 compositions are prepared by combining the adhesive material and water in an appropriate container, and mixing the combination at 400–600 rpm until all of the materials are well dispersed. The agitation is then increased as silica and talc are added. The agitation is continued until all materials dispersed in solution.

TABLE 2

Topical Liquid Compositions

| Ingredient | | 2.1 | 2.2 | 2.3 | 2.4 | 2.5 |
|---|---|---|---|---|---|---|
| Luviflex Soft | Acrylates Copolymer | 6.0 | — | — | — | — |
| Polyderm PE/PA | Polyether Propionic Acid/TMX Copolymer | — | 6.0 | — | — | — |
| Luviset PUR | Polyurethane-1 | — | — | 6.0 | — | — |
| Luviskol K90 | PVP | — | — | — | 6.0 | — |
| Eastman AQ 38S | Diglycol/CHDM/Isophthalates/SIP Copolymer | — | — | — | — | 6.0 |
| Silica Shells | Silica | 2.0 | 2.0 | 2.0 | 2.0 | 2.0 |
| Talc USP | Talc | 18.0 | 18.0 | 18.0 | 18.0 | 18.0 |
| Water | — | 60 | 60 | 60 | 73.9 | 74 |

Each of the Table 2 compositions are prepared by combining the adhesive and water in an appropriate container, and then mixing the combination at 400–600 rpm until all such materials are well dispersed. The agitation is increased as the other ingredients are added, and is continued until all materials are dispersed in solution.

TABLE 3

Topical Liquid Compositions

| Ingredient | | 3.1 | 3.2 | 3.3 | 3.4 | 3.5 |
|---|---|---|---|---|---|---|
| Diahold JG (60% in IDD) | Acrylates Copolymer | 6.0 | — | — | — | — |
| Amphomer LV-71 | Octylacrylamide/Acrylates/Butylaminoethyl methacrylate Copolymer | — | 6.0 | — | — | — |
| SA 70 (23% in D5) | Polyacrylates-g-polysiloxane copolymer | — | — | 6.0 | — | — |
| Bio-PSA (40% in IDD) | Trimethylated silica treated with dimethyl siloxane (silicone resin copolymer) | — | — | — | 6.0 | — |
| Dermacryl LT | Acrylates/Octylacrylamide Copolymer | — | — | — | — | 6.0 |
| Pemulen TR2 | Acrylates/C10–30 Alkyl Acrylate Crosspolymer | 0.3 | — | 0.3 | 0.3 | — |
| AMP-Regular | aminomethylpropanol | * | 1.31 | * | * | 1.14 |
| Silica Shells | Silica | 2.0 | 2.0 | 2.0 | 2.0 | 2.0 |
| Talc USP | Talc | 18.0 | 18.0 | 18.0 | 18.0 | 18.0 |
| Water | — | 69.7 | 68 | 68 | 69.4 | 65 |

*Amp as needed for pH adjustment

Each of the Table 3 compositions are prepared by combining Pemulen and water in an appropriate container, and then mixing the combination at 400–600 rpm until all materials are well dispersed. The adhesive is added with agitation until well dispersed. The AMP is titrated to a composition pH of 6. The agitation of the mixture is increased as the other materials are added, and the agitation continued until all materials are well dispersed in solution.

TABLE 4

Topical Liquid compositions

| Ingredient | | 4.1 | 4.2 |
|---|---|---|---|
| Amphomer LV-71 | Octylacrylamide/Acrylates/Butylaminoethyl methacrylate Copolymer | 6.0 | — |
| Dermacryl LT | Acrylates/Octylacrylamide Copolymer | — | 6.0 |
| AMP-Regular | Aminomethylpropanol | 1.31 | 1.14 |
| Silica Shells | Silica | 2.0 | 2.0 |
| Talc USP | Talc | 18.0 | 18.0 |
| Water | — | 69.7 | 68 |

Each of the Table 4 compositions is prepared by combining the adhesive material and water in appoprtiate container, and then mixing the combination at 400–600 rpm until all materials are well dispersed. The AMP is then added to the combination with mixing. The agitation is then increased as the other ingredients are added. The agitation is maintained until all of the materials in the composition are well dispersed in solution.

TABLE 5

Topical Liquid Compositions

| Ingredient | | 5.1 | 5.2 | 5.3 |
|---|---|---|---|---|
| Bio PSA 4500 (40% in IDD) | Trimethylated silica treated with dimethyl siloxane, Isododecane | 4.0 | 4.0 | 4.0 |
| Pemulen TR2 | Acrylates/C10–30 Alkyl Acrylate Crosspolymer | 0.3 | 0.3 | 0.3 |
| Aerosil 325 | Fumed Silica | — | — | 2.0 |
| Snowtex UP | Colloidal Silica | — | 2.0 | — |

TABLE 5-continued

Topical Liquid Compositions

| Ingredient | | 5.1 | 5.2 | 5.3 |
|---|---|---|---|---|
| Syloid 244 | Precipitated silica | 2.0 | — | — |
| Tapioca Pure | Tapioca starch | 11.8 | 11.8 | 11.8 |
| Talc USP | Talc | 2.0 | 2.0 | 2.0 |
| Fragrance | Fragrance | 0.6 | 0.6 | 0.6 |
| Ethanol, Denatured 190 Proof | Ethanol | 0.25 | 0.25 | 0.25 |
| Ethanol, Denatured 190 Proof | Ethanol | 30.0 | 30.0 | 30 |
| Stepan 1PM | Isopropyl Myristate | 5.0 | 5.0 | 5.0 |
| Water | — | | 35.6 | 27.6 | 35.6 |

Each of the Table 5 compositions is prepared by combining Pemulen and water in an appropriate container, and then mixing the combination at 400–600 rpms until all of the materials are well dispersed. The adhesive, IPM, and silica are then added to the composition with agitation. The aminomethylpropanol is then added to the composition until the pH of the composition reaches 7.5. The agitation is then increased and other materials are each added slowly to the composition. Agitation continues until all of the ingredients are well dispersed.

What is claimed is:

1. A method of absorbing sweat and sebum from the skin, said method comprising the topical application to the skin of a liquid composition comprising:
   (A) fluid-absorbent solids having a Water Absorption Value of at least about 0.5 gram/gram;
   (B) an adhesive fluid; and
   (C) a liquid carrier,
wherein the topical composition has a Average Wear Index of at least about 25%.

2. The method of claim 1, wherein the fluid-absorbent solids have a Water Absorption Value of from about 1.0 to about 5.0.

3. The method of claim 1, wherein the fluid-absorbent solids are selected from the group consisting of silicas, silicates, carbonates, fluid-absorbent polymers, and combinations thereof.

4. The method of claim 1, wherein the fluid-absorbent solids are selected from the group consisting of calcium silicates, amorphous silicas, calcium carbonate, magnesium carbonate, zinc carbonate, magnesium silicate, starch, microcrystalline cellulose, and combinations thereof.

5. The method of claim 1, wherein the fluid-absorbent solids represent from about 0.5% to about 20% by weight of the topical liquid composition.

6. The method of claim 1, wherein the topical liquid composition has an Average Wear Index is from about 75% to 100%.

7. The method of claim 1, wherein the adhesive fluid comprises a silicone-containing adhesive.

8. The method of claim 7, wherein the silicone-containing adhesive comprises a silicone resin copolymer.

9. The method of claim 8 wherein the silicone resin copolymer has an average molecular weight of at least about 15,000, and wherein the silicone resin copolymer is a condensation product of an organosiloxane resin and a diorganosiloxane fluid.

10. The method of claim 9 wherein the silicone resin copolymer has an average molecular weight of from about 100,000 to about 3 million.

11. The method of claim 9 wherein the diorganosiloxane fluid is a hydroxyl end blocked diorganopolysiloxane having a viscosity of from about 100 to about 100,000 cs at 25° C., and wherein the organic substituents on the diorganopolysiloxane fluid are selected from the group consisting of methyl, ethyl, and vinyl radicals.

12. The method of claim 11 wherein the silicone resin is as a condensation product of $SiO_2$ and $R_3(SiO)_{0.5}$ units; wherein each R group is independently selected from the group consisting of methyl, ethyl, propyl and vinyl radicals; and the molar ratio of $SiO_2$ units to $R_3(SiO)_{0.5}$ units in the silicone resin is from about 0.6 to about 1.0.

13. The method of claim 10 wherein the silicone resin copolymer represents from about 0.05% to about 40% by weight of the composition.

14. The method of claim 7, wherein the silicone-containing adhesive comprises an organosiloxane resin in combination with a diorganosiloxane fluid.

15. The method of claim 14 wherein the weight ratio of the organosiloxane resin to the diorganopolysiloxane fluid is from about 1:5 to about 10:1.

16. The method of claim 15 wherein the weight ratio of the oranosiloxane resin to the diorganopolysiloxane fluid is from about 1:1 to about 3:1.

17. The method of claim 14 wherein concentration of the combination of the organosiloxane resin and the diorganopolysiloxane fluid is from about 10% to about 40% by weight of the composition.

18. The method of claim 14 wherein the diorganosiloxane fluid is a polydiemethylsiloxane fluid having a viscosity at 25° C. of from about 100,000 to about 25,000,000 centistokes (cSt) at 25° C.

19. The method of claim 1, wherein the liquid carrier comprises a non-volatile residue masking agent.

20. The method of claim 1, wherein the composition is intended solely for rinse-off application.

21. The method of claim 1, wherein the composition further comprises from about 0.1% to about 5% by weight of a fragrance.

22. The method of claim 1, wherein the composition is substantially free of pigments.

23. The method of claim 1, wherein the composition is not intended for topical application to the bead or neck.

24. The method of claim 1, wherein the fluid-absorbing solids have an average particle size of less than about 250 nm.

25. Topical liquid compositions comprising:
   (A) fluid-absorbent solids having a Water Absorption Value of at least about 0.5 gram/gram;
   (B) an adhesive fluid; and
   (C) a liquid carrier;
wherein the topical composition has a Average Wear Index of at least about 25%.

26. A topical liquid composition according to claim 25, wherein the fluid-absorbent solids have a Water Absorption Value of from about 1.0 to about 5.0.

27. A topical liquid composition according to claim 25, wherein the fluid-absorbent solids are selected from the group consisting of silicas, silicates, carbonates, fluid-absorbent polymers, and combinations thereof.

28. A topical liquid composition according to claim 25, wherein the fluid-absorbent solids are selected from the group consisting of calcium silicates, amorphous silicas, calcium carbonate, magnesium carbonate, zinc carbonate, magnesium silicate, starch, microcrystalline cellulose, and combinations thereof.

29. A topical liquid composition according to claim 25, wherein the fluid-absorbent solids represent from about 0.5% to about 20% by weight of the topical liquid composition.

30. A topical liquid composition according to claim 25, wherein the topical liquid composition has an Average Wear Index is from about 75% to 100%.

31. A topical liquid composition according to claim 25, wherein the adhesive fluid comprises a silicone-containing adhesive.

32. A topical liquid composition according to claim 25, wherein the silicone-containing adhesive comprises a silicone resin copolymer.

33. The liquid composition of claim 32 wherein the silicone resin copolymer has an average molecular weight of at least about 15,000, and wherein the silicone resin copolymer is a condensation product of an organosiloxane resin and a diorganosiloxane fluid.

34. The liquid composition of claim 33 wherein the silicone resin copolymer has an average molecular weight of from about 100,000 to about 3 million.

35. The liquid composition of claim 33 wherein the diorganosiloxane fluid is a hydroxyl end blocked diorganopolysiloxane having a viscosity of from about 100 to about 100,000 cs at 25° C., and wherein the organic substituents on the diorganopolysiloxane fluid are selected from the group consisting of methyl, ethyl, and vinyl radicals.

36. The liquid composition of claim 35 wherein the silicone resin is as a condensation product of $SiO_2$ and $R_3(SiO)_{0.5}$ units; wherein each R group is independently selected from the group consisting of methyl, ethyl, propyl and vinyl radicals; and the molar ratio of $SiO_2$ units to $R_3(SiO)_{0.5}$ units in the silicone resin is from about 0.6 to about 1.0.

37. The liquid composition of claim 34 wherein the silicone resin copolymer represents from about 0.05% to about 40% by weight of the liquid composition.

38. The liquid composition of claim 31, wherein the silicone-containing adhesive comprises an organosiloxane resin in combination with a diorganosiloxane fluid.

39. The liquid composition of claim 38 wherein the weight ratio of the organosiloxane resin to the diorganopolysiloxane fluid is from about 1:5 to about 10:1.

40. The liquid composition of claim 39 wherein the weight ratio of the oranosiloxane resin to the diorganopolysiloxane fluid is from about 1:1 to about 3:1.

41. The liquid composition of claim 39 wherein concentration of the combination of the organosiloxane resin and the diorganopolysiloxane fluid is from about 10% to about 40% by weight of the composition.

42. The liquid composition of claim 39 wherein the diorganosiloxane fluid is a polydiemethylsiloxane fluid having a viscosity at 25° C. of from about 100,000 to about 25,000,000 centistokes (cSt) at 25° C.

43. A topical liquid composition according to claim 25, wherein the liquid carrier comprises a non-volatile residue masking agent.

44. A topical liquid composition according to claim 25, wherein the composition is intended solely for 25, rinse-off application.

45. A topical liquid composition according to claim 25, wherein the composition further comprises from about 0.1% to about 5% by weight of a fragrance.

46. A topical liquid composition according to claim 25, wherein the composition is substantially free of pigments.

47. A topical liquid composition according to claim 25, wherein the composition is not intended for topical application to the head or neck.

48. A topical liquid composition according to claim 25, wherein the fluid-absorbing solids have an average particle size of less than about 250 nm.

* * * * *